(12) United States Patent
Marple et al.

(10) Patent No.: US 6,453,758 B1
(45) Date of Patent: Sep. 24, 2002

(54) EFFICIENT HIGH-PRODUCTIVITY CASCADE IMPACTORS

(75) Inventors: Virgil A. Marple, Maple Plain; Daryl L. Roberts, Blaine; Benjamin Y. H. Liu, North Oaks, all of MN (US)

(73) Assignee: MSP Corporation, Minneapolis, MN (US)

( * ) Notice: Subject to any disclaimer, the term of this patent is extended or adjusted under 35 U.S.C. 154(b) by 0 days.

(21) Appl. No.: 09/567,552

(22) Filed: May 5, 2000

Related U.S. Application Data

(60) Provisional application No. 60/138,742, filed on Jun. 11, 1999.

(51) Int. Cl.⁷ ................................................. G01N 1/00
(52) U.S. Cl. ......................... 73/863.22; 55/318; 55/319; 209/133
(58) Field of Search ................................. 209/659, 680, 209/133, 138, 139.1, 140, 141, 145; 55/315, 319, 342, 392, 394, 395, 396, 400, 401, 462; 73/28.01, 28.04, 28.05, 863.22, 863.41

(56) References Cited

U.S. PATENT DOCUMENTS

| | | | |
|---|---|---|---|
| 2,538,116 A | 1/1951 | May ............................... 73/28 |
| 3,127,763 A | 4/1964 | Lippmann ........................ 73/28 |
| 3,518,815 A | 7/1970 | McFarland et al. ............ 55/241 |
| 3,693,457 A | 9/1972 | Pilat .............................. 73/28 |
| 4,133,202 A | 1/1979 | Marple .......................... 73/28 |
| 4,255,172 A | * 3/1981 | Smith .......................... 55/270 |
| 4,274,846 A | 6/1981 | Smith .......................... 55/270 |
| 4,321,822 A | * 3/1982 | Marple et al. .................. 73/28 |
| 4,391,151 A | 7/1983 | Nelson et al. ............ 73/863.23 |
| 4,400,982 A | 8/1983 | Bell ........................ 73/863.22 |
| 4,452,068 A | 6/1984 | Loo ................................ 73/28 |
| 4,463,595 A | 8/1984 | Yeh et al. ....................... 73/28 |
| 4,523,990 A | 6/1985 | Duyckinck .................. 209/138 |
| 4,570,494 A | 2/1986 | Dunn et al. .............. 73/863.22 |
| 4,640,140 A | 2/1987 | Burghoffer et al. ....... 73/863.22 |
| 4,725,294 A | 2/1988 | Berger .......................... 55/270 |
| 4,764,186 A | 8/1988 | Langer .......................... 55/17 |
| 4,827,779 A | 5/1989 | Marple et al. ........... 73/863.22 |
| 4,972,957 A | 11/1990 | Liu et al. .................... 209/143 |
| 5,201,231 A | 4/1993 | Smith ...................... 73/863.22 |
| 5,343,767 A | 9/1994 | Marple et al. ........... 73/863.22 |
| 5,437,198 A | 8/1995 | John ....................... 73/863.22 |
| 5,693,895 A | 12/1997 | Baxter ..................... 73/863.22 |

FOREIGN PATENT DOCUMENTS

| | | | |
|---|---|---|---|
| DE | 2832238 A | 2/1979 | |
| DE | 3110871 | 10/1982 | .......... G01N/15/02 |
| DE | 3545120 | 7/1986 | .......... G01N/15/06 |
| GB | 1354261 | 5/1974 | .......... B01D/45/04 |
| GB | 2179273 | 3/1987 | .......... B07B/7/04 |
| GB | 2 179 273 A | * 3/1987 | .......... B07B/7/04 |
| JP | 560760 A | 6/1981 | |

* cited by examiner

*Primary Examiner*—Donald P. Walsh
*Assistant Examiner*—Mark J Beauchaine
(74) *Attorney, Agent, or Firm*—Westman, Champlin & Kelly, P.A.

(57) ABSTRACT

A compact cascade impactor is formed to classify particles carried in a flow through the impactor. The impactor has collection chambers that are arranged to conserve space and yet provide a large flow passageway. The collection chamber may be tear drop shaped and being nested together. The impactor includes nozzles that are used across a desired flow range without changing the nozzles.

25 Claims, 15 Drawing Sheets

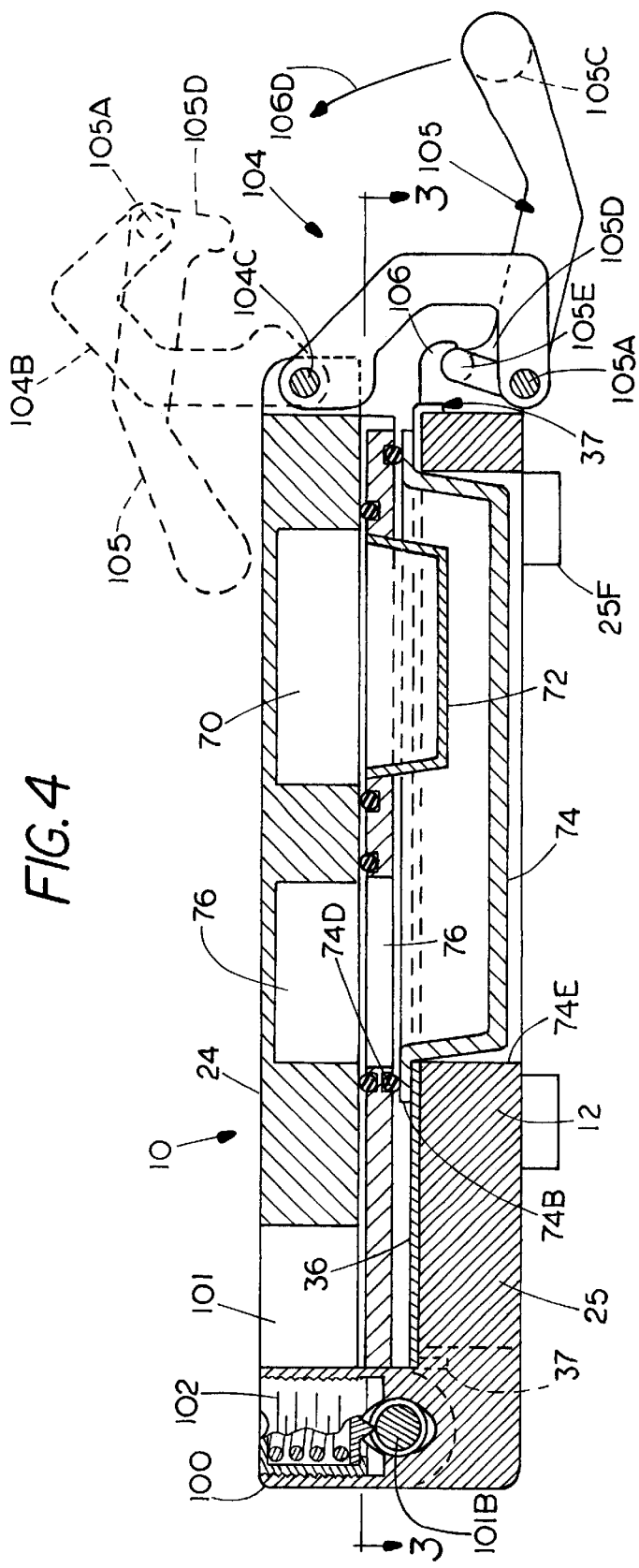

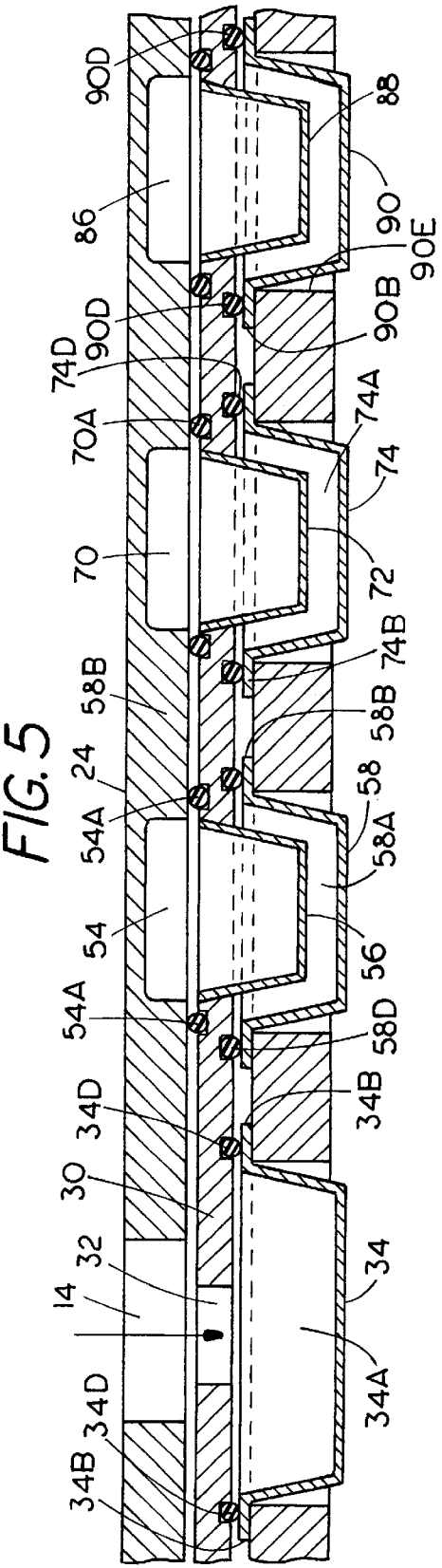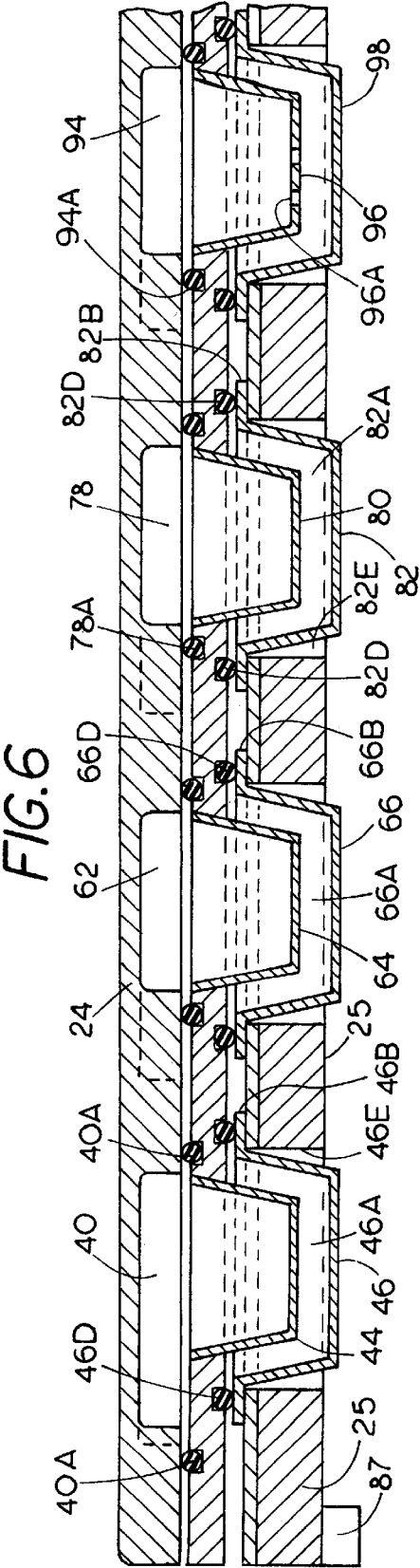

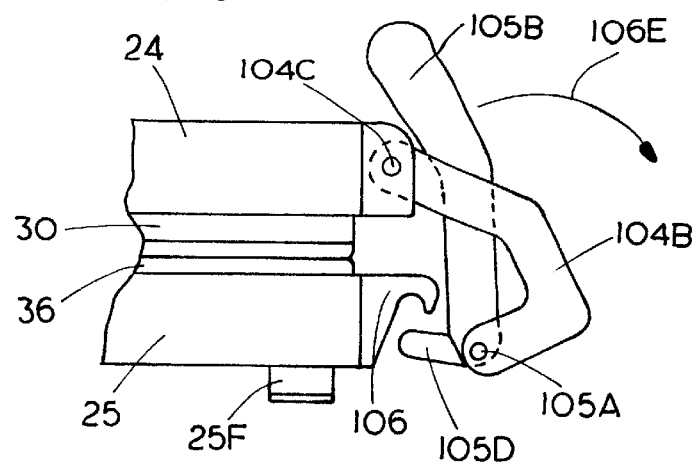
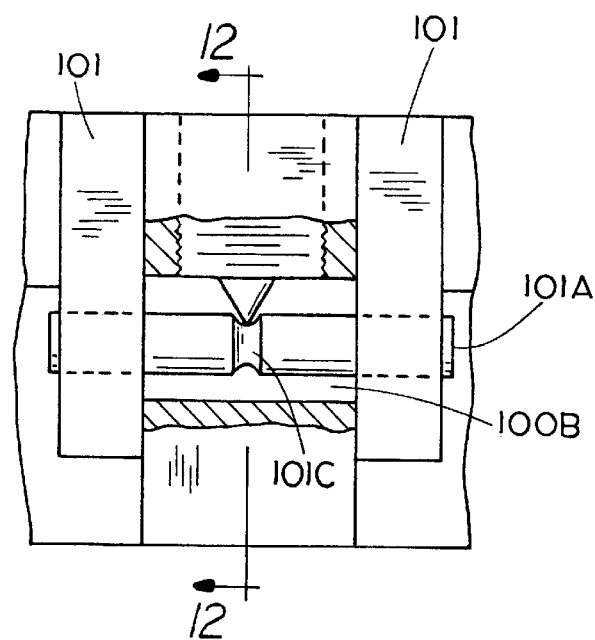
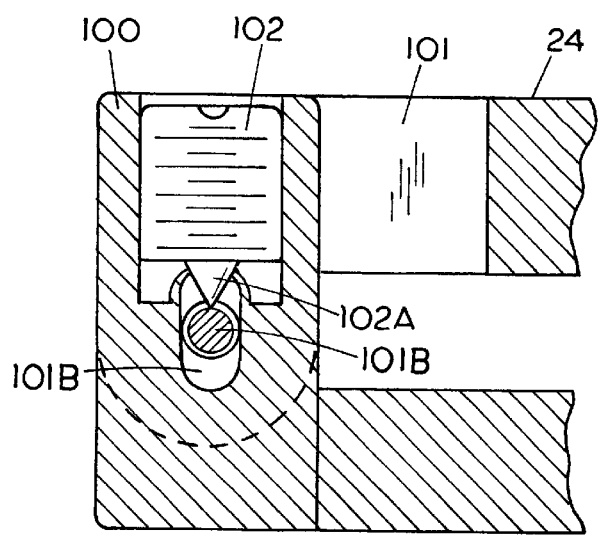

US 6,453,758 B1

EFFICIENT HIGH-PRODUCTIVITY CASCADE IMPACTORS

CROSS REFERENCE TO RELATED APPLICATION

This application claims priority on provisional application Ser. No. 60/138,742, filed Jun. 11, 1999 for COMPACT, HIGH-PRODUCTIVITY CASCADE IMPACTORS.

BACKGROUND OF THE INVENTION

The present invention relates to a particle impactor used for classifying particles according to size for analysis of the particles carried in a gas flow. Sharp particle cutoff is obtained, with compactly arranged impactor/collection cups and flow channels for conserving space, and providing accurate information about the particles.

Various types of impactors have been utilized in the prior art, including devices that use cascading elements for obtaining a classification of particles. Generally a cascade impactor has a plurality of collection stages arranged in series, with each stage having a nozzle or orifice plate with nozzle openings smaller in size than those of the previous stage, and also having an impaction surface for the collection of the particles that are too large to be carried farther in the fluid stream. At the smaller nozzle openings, the velocity of the fluid carrier is higher, and the particles have a higher velocity moving through the nozzle. The higher the flow velocity through the nozzle, the smaller the particles that are collected on the impaction plate. In other words, particles larger than the cut size of an impactor will impinge upon the impaction surface and the rest of the particles will pass with the fluid or airstream to the next stage. The particles that are collected at each stage can be analyzed by weight, or by quantitative chemical analysis. When the particles are to be chemically analyzed, it is desirable to collect the particles in a container or cup so the particles easily can be transported to a lab for analysis.

Another problem that arises with impactors is loss of particles due to the collection of some particles on surfaces other than the particle impactor surface, the collection on surfaces other than the impactor surface results in losses and these are called interstage particle loss. Minimizing such interstage particle loss is a desirable feature of the present invention

SUMMARY OF THE INVENTION

The present invention relates to a compact, high productivity cascade impactor that is easily used, manually or with a robot system and which provides for a broad flow range with quite precise particle cutoff sizes at the various stages. The physical construction makes the impactors of the present invention easily automated, and the usual final filters can be eliminated from the system and a microporous plate filter provided to avoid errors that may arise by contaminants on conventional filters.

The interstage passageways and the nozzles are designed so that they have low particle losses. The impactors thus are acceptable to regulators, such as the Food and Drug Administration and the British and European equivalents.

The impactor preferably has cups that are supported on a tray or frame. The cup tray and all the cups can be removed as a separate unit for quantitative recovery of material from the cups. The cup shape is chosen to reduce the space occupied by the impactor while not compromising the aerodynamic performance of the impactor.

A preferred form of the invention conserves space by utilizing teardrop shaped interstage passageways and collection cups. Other forms include stacked impactors, in order to provide for unique and compact units. The impactors are preferably constructed of inert materials, and are physically robust, and since they are metal and can be grounded they are unaffected by static.

The present invention is made with one set of fixed nozzles to achieve the desired range of particle size cut points, from about 0.5 $\mu$m to 10 $\mu$m at seven different cut points. At any flow rate, five or more of these are within the range desired for assessing the safety and efficacy of the drug formulation. The impactor is designed to accept a wide range of flows, for example between 30 liters per minute and 100 liters per minute, which is the typical flow range for testing inhalables as described in the United States Pharmacopoeial (USP) or corresponding British, European or Japanese Pharmacopoeials.

BRIEF DESCRIPTION OF THE DRAWINGS

FIG. 4 is a sectional view taken as on line 4—4 in FIG. 3;

FIG. 5 is a sectional view taken as on line 5—5 in FIG. 3;

FIG. 6 is a sectional view taken as on line 6—6 in FIG. 3;

FIG. 10 is a fragmentary side view of a latch in position about to close;

FIG. 11 is an enlarged rear view of a typical cover hinge;

FIG. 12 is a sectional view taken on line 12—12 in FIG. 11;

DETAILED DESCRIPTION OF THE ILLUSTRATIVE EMBODIMENTS

Figure 1:
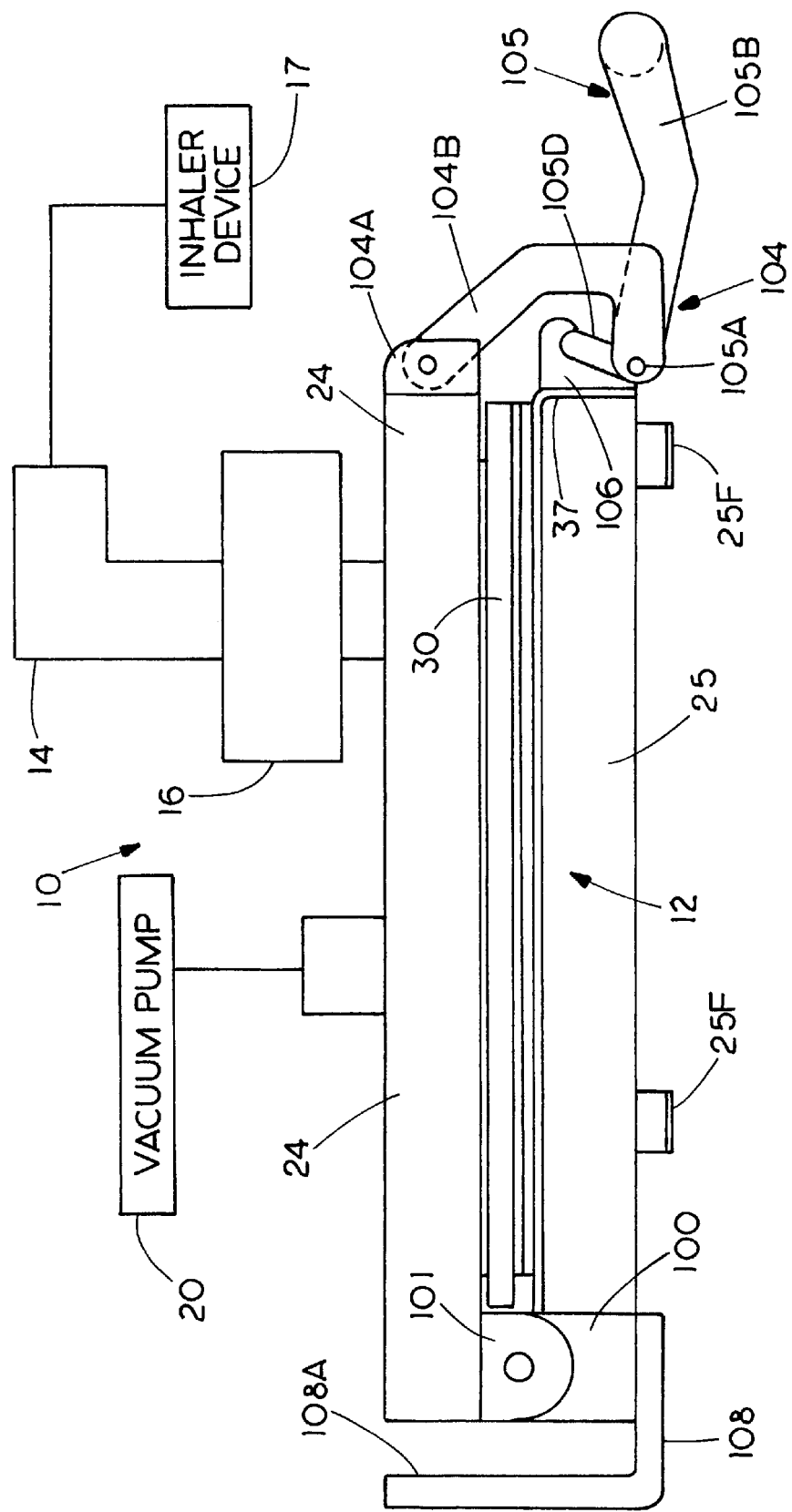
FIG. 1 is a side view of an impactor made according to the present invention.

A first form of the invention illustrated in FIGS. 1 through 9 comprises an impactor assembly 10, which has a housing assembly 12, with an aerosol inlet 14 of standard size described in USP 24, Section 601. The inlet can be a standard USP type inlet tube. A pre-separator 16 is illustrated on the inlet in FIG. 1, and it is used to separate out large particles with a standard type impactor arrangement. The pre-separator is also shown in detail in FIGS. 8 and 9.

The aerosol that is passed through the impactor 10 is an aerosol generated by a hand-held inhaler 17 or other device that may be a liquid or dry powder drug inhaler, such as those used to control asthma and similar problems. The amount of flow from each charge is small, so the internal volume of the impactor 10 must be kept low. For testing dry powder inhalers, accepted methods call for the total volume of sampled air to be between 2 liters and 4 liters. Therefore, the internal volume of the impactor must be low to achieve proper particle sizing. The internal volume or dead volume is preferably 1 to 2.5 liters. Small dead volume is important for achieving steady state flow during a typical breath volume of 2 to 4 liters. Steady state flow is achieved in about 0.2 seconds. The entire test is completed in 2 to 4 seconds. The flow rate through the impactor will be generated in a selected manner, for example by providing a vacuum pump such as that shown at 20 on an exhaust or flow outlet opening 22 from the impactor housing 12.

The impactor 10 of the first form of the invention is made to be compact so that it is easily used, portable and does not take up much space, and can be operated in a normal manner. The impactor 10 of the first form of the invention has a lid or cover 24 that is sufficiently thick to include flow passageways on the underside. The lid or cover 24 has the inlet 14 at one and thereof. The lid or cover 24 is hinged along one edge to a base frame 25 that has a number of egg shaped or teardrop shaped openings that receive and support impactor particle collection chambers or cups as will be shown.

As shown in FIGS. 3, 4, 5 and 6 a seal plate 30 is positioned just below the cover of lid 24 and as will be explained, has seals on both sides to seal passageways on the underside of the cover and, on the opposite or bottom side of the seal plate 30, to seal around lips of each of the impaction chambers or cups to define sealed passageways for forming the flow path. The collection chambers or cups will be individually numbered in this description, but the first cup at the inlet is shown at 34, and is larger than the rest. Inlet opening 14 in cover 24 opens through an inlet opening 34 that sealingly opens through the seal plate 30 and cover or lid 24 into a chamber or passageway 34A defined by a first impaction stage cup 34. Cup 34 fits through an opening in a cup retainer tray or frame 36. The tray or frame 36 is supported on the top of the base frame 25. The cup 34 has a peripheral flange 34B that rests on the tray 36. The cup also fits in an opening 34E in the base frame 25.

The impaction cups are tear drop shaped as shown. The large end 34E of the first stage cup forms the impactor surface and underlies the inlet opening 32. The flange 34B of the cup 34 is sealed with a seal 34D on the seal plate and extends transversely of the impactor to a vertical passageway 38 that opens through the seal plate 30 to interface or crossover passage 40 formed on the underside of the cover 24.

Figure 3:
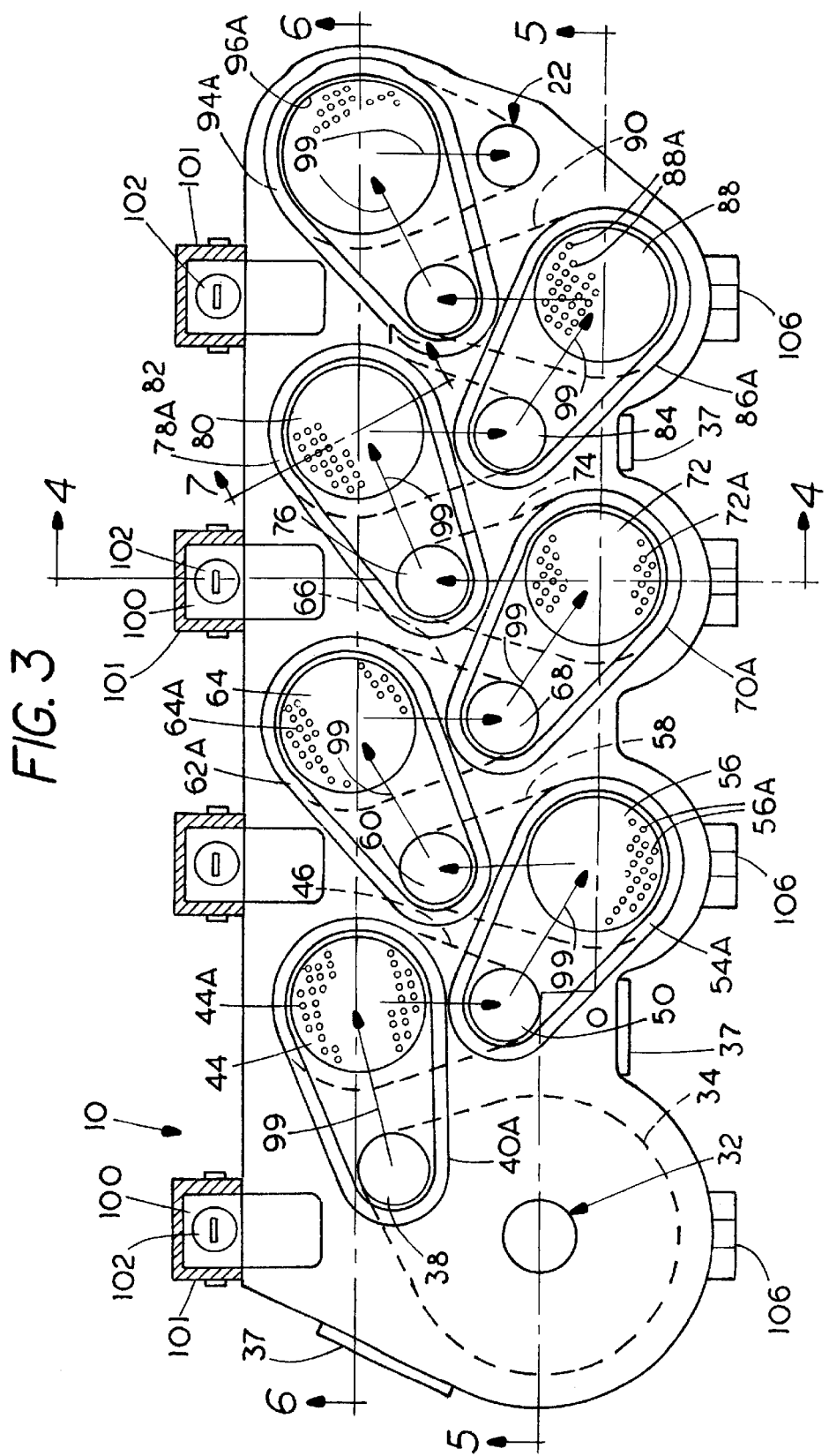
FIG. 3 is a top plan view thereof with the top cover removed.
Figure 3A:
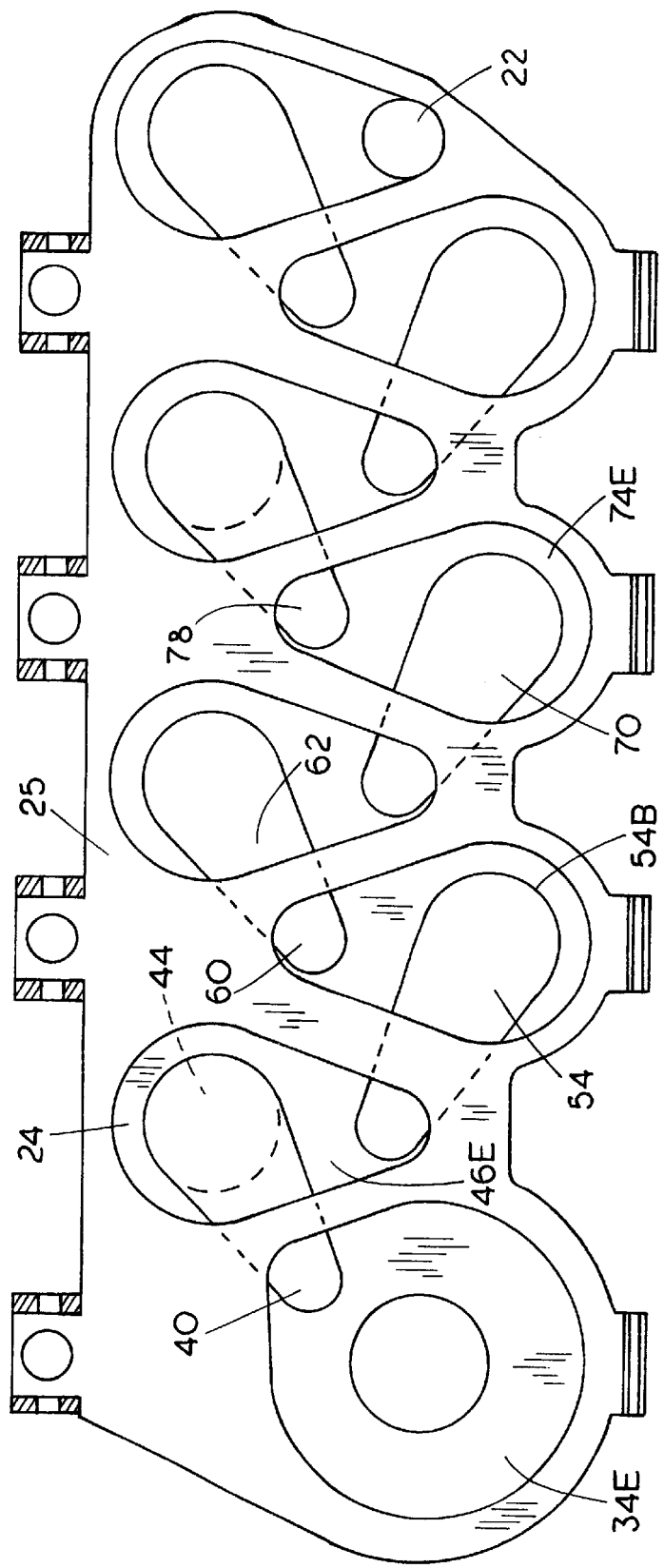
FIG. 3A is a bottom plan view of the impactor with a seal plate removed and showing passageways in a cover through openings in the base and with other parts removed.

FIG. 3A is a bottom view of the base frame 25, with the cups and seal plate removed, so the interstage passages on the underside of the cover 24 can be seen. The openings in the cups on the base frame 25 are designated with the cup member followed by the letter "E". The seals on the periphery of the cups follow the shape of the cup openings in base frame 25 shown in FIG. 3A, and as shown in dotted lines in FIG. 3.

The crossover or interstage passageway 40 leads to a nozzle passageway or opening in seal plate 30 (FIGS. 3 and 6) having a nozzle 44 that has openings 44A of desired size, and desired number as will be shown in Table I, so that particles passing through the nozzle 44 will be accelerated and will discharge into a second stage impactor surface of a cup 46 that underlies the nozzle 44. The interstage passageway 40 in the cover 24 is sealed with a seal 40A (FIG. 3). The nozzle thus is downwardly directed toward an underlying impaction surface. The tear drop shaped cup 46 has a wide end under the nozzle and a narrow opposite end. The cup 46 forms an impactor chamber that defines a passageway 46A that extends laterally across the seal plate 30. The flange 46B of the cup 46 is sealed with seal 46D, that encircles the cup. The cup is positioned in opening 46E of the base frame 25. The small end of the cup 46 aligns with a vertical passageway or port 50 that extends through the seal plate and opens into a crossover or interstage passage 54 in the cover 24. The opening 46E in the base frame 25 shown in FIG. 3 shows the shape of the cup 46 and passageway 46A.

The crossover or interstage passageway 54 is also tear drop shaped as can be seen in FIGS. 3 and 3A, and the large end 54B of passageway 54 overlies an opening in seal plate 30 which holds a nozzle 56 that has openings 56A therein. The interstage passageway 54 is sealed with a seal 54A. The openings 56A are smaller and greater in number than the opening 44A in nozzle 44. The nozzle 56 overlies a third stage impactor surface of a cup 58. The third stage impactor cup 58 is also tear drop shaped and forms a passageway 58A (see FIGS. 3, 3A and 5) that extends laterally back in direction toward the hinge side of the base frame 25 and opens to a vertical passageway 60 through the seal plate 30 that connects to a crossover or interstage passageway 62 in the cover 24. The seal plate 30 has a seal 58D that seals on flange 58B of cup 58.

The crossover passage 62 also is tear drop shaped, and the large end of the crossover passage 62 opens downwardly through an opening in seal plate 30 which holds a nozzle 64 which has a selected number of openings 64A. The interstage or crossover passageway 62 is sealed with a seal 62A.

Nozzle 64 opens to a underlying cup 66 that again is tear drop shaped and provides a fourth stage impactor surface at its larger end. The cup 66 has a flange 66B sealed with a seal 66D and forms a passageway 66A that extends laterally back across the base frame 25 to a vertical port or passageway 68 through seal plate 30 that connects to a crossover or interstage passageway 70 in the cover 24. Passageway 70 has a larger end that opens through an opening in the seal plate 30 supporting a nozzle 72 with openings 72A. The interstage passageway 70 is sealed with a bounding seal 70A.

A cup 74 providing a fifth stage impactor and has an impactor surface at its large end that underlies the nozzle 72 and forms a passageway 74A that extends laterally back across the base frame 25 to a vertical port or opening 76 through the seal plate 30. The cup 74 has a peripheral flange 74B that is sealed with a peripheral seal 74D. The opening 76 connects to a crossover or interstage passageway 78 in the underside of cover 24. The opening 74E in the base frame 25 shown in FIG. 3A is for cup 74 and shows the shape of the cups 74, looking from the bottom up. Cups 66 and 74 are also shown in FIG. 5, where the cover and seal plate are broken away.

The crossover passageway 78 is tear drop shaped and opens to a nozzle supporting opening in the seal plate 30 having a nozzle 80 therein, with openings 80A that provides for a flow downwardly into an underlying sixth stage impactor cup 82 in an opening 82E in base 25. The nozzle 80 is retained in place with a rim 80D. The interstage passageway 78 is sealed with a seal 78A on seal plate 30. The cup 82 forms an impaction chamber and passageway 82A. The cup 82 is tear drop shaped and has an impaction surface at its large end. The cup 82 has a flange 82B supported on the cup tray, and a peripheral seal 82D on the seal plate seals around the cup. The cup 82 extends over to an opening or passageway 84 that leads through the seal plate 30 to a crossover interstage passageway 86 in the underside of cover 24 that forms a passageway section for carrying flow.

The crossover or interstage passageway 86 is sealed with a seal 86A on seal plate 30. The passageway 86 leads to an opening in seal plate 30 that has a further nozzle 88 that has openings 88A that open to an underlying cup 90 forming a seventh impaction stage. The cup 90 is tear drop shaped and forms a passageway 90A that extends laterally to a vertical opening 92 through seal plate 30 that leads to crossover or interstage passageway 94 in the cover 24. The cup 90 has a flange 90B that is sealed with a seal 90D on the seal plate. The flange 90B is shaped like opening 90E, and rests on the cup tray 36, as to all of the cups.

The passageway 94 opens to a final stage micro orifice filter nozzle 96 supported in an opening in the seal plate 30. The passageway 94 is sealed with a seal 94A on the seal plate that has openings 96A and which discharges the fluid into an underlying cup 98 that is tear drop shaped and opens to the fluid flow outlet passage 22 from the impactor.

Figure 7:
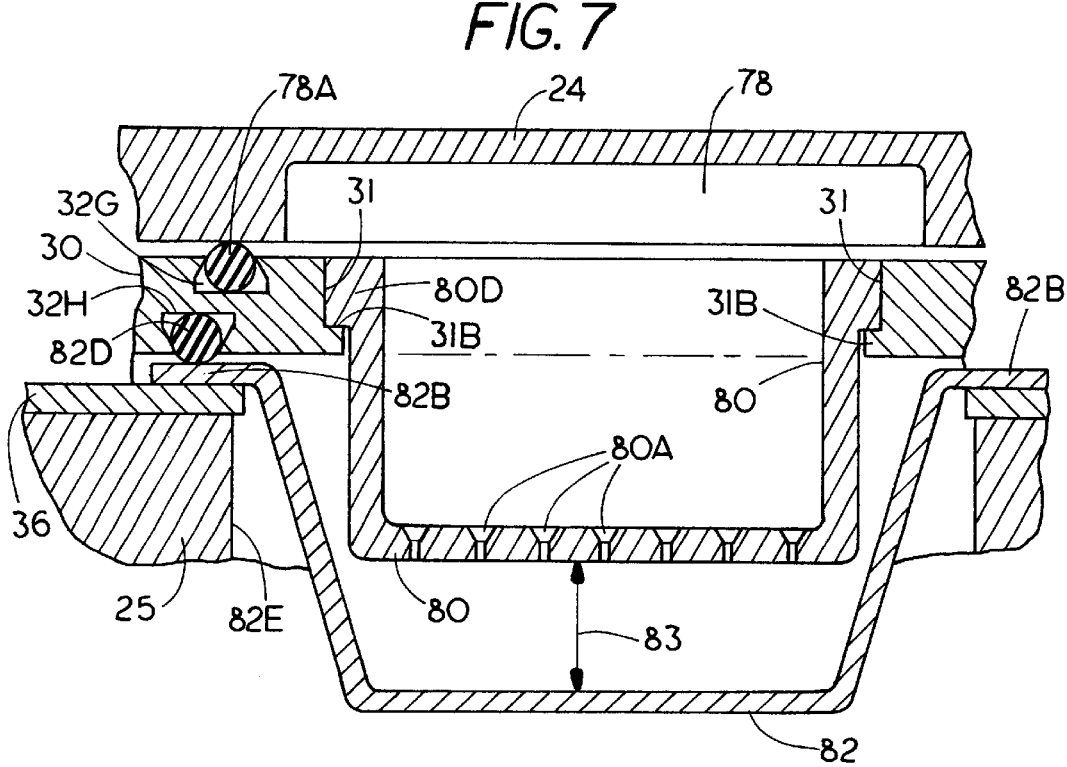
FIG. 7 is an enlarged sectional view taken on line 7—7 in FIG. 3.

In FIG. 7 a detailed enlarged showing of a typical way of mounting a nozzle in the seal plate is illustrated. In this instance, the nozzle 80 is illustrated, and FIG. 7 is taken along line 7—7 in FIG. 3.

The seal plate 30, as shown, and as was explained has "O" ring type seals thereon. The seal 78A is illustrated on the top side of the seal plate, against the surface of the cover 24, and a seal 82D is shown against the flange 82B of the cup 82. The seal receiving grooves that are formed in the seal plate 30 are shown at 32G and 32H, respectively, and are shaped so that they will permit the seals 78A and 82D, which are suitable durometer rubber, to spread slightly as the cover 24 is loaded against the seals and then the seal plate is loaded against the flange 82B, which in turn is supported by the cup tray 36. The cup tray 36 is supported on the base 25.

Each of the nozzle holders is formed with a sealing rim typically shown at 80D in FIG. 7 and is positively seated in an opening 31 in the seal plate 30 against a shoulder 31B, so that the distances from the nozzle to the cup such as that shown at 83 are precisely maintained. The nozzles are made so the rim and side walls are machined from a single block of material. The actual nozzle plate having the nozzle opening will be machined on the nozzles with larger openings. When small openings are needed, the nozzles are two pieces assembled together. The bottom wall or plate can be made by other processes to get the small holes needed. Then it can be brazed or otherwise sealingly secured to the lower end of the nozzle holder.

Also, the nozzle sealing along the surface 31 insures that there will be no flow leakage, and with the seals carried by the seal plate, which will expand into the grooves when compressed, positively sealing of each of the passageways, and on the cups along the cup flanges is maintained.

The cover 24 is hinged to the base with a hinge. As shown, a pin that is spring loaded is provided to permit some desired resilient movement perpendicular to the seal plate to provide compression of the seals on the seal plate 30. As shown in FIGS. 2, 4, 10, 11 and 12, the hinging between the cover 24 and the base 25 may be made so that as compression of the seals on the seal plate 30 occurs, the surfaces that engage the seal plate, namely the lips on the cups and the under surface of the cover, remain parallel.

As shown, the base frame 25 has a plurality of upright hinge posts 100, that are spaced along the hinging edge of the base frame and cover, and the cover has sets of flanges 101, that fit on the opposite sides of the posts 100. The flanges 101 carry a pivot pin 101A that passes through a slot 100B in each of the upright posts 100. The pivot pin 101B can move up and down in the slot 100B, shown in FIGS. 11 and 12, and the pin is urged downwardly with a spring loaded, threaded plunger 102 that is threaded into a bore in the respective hinge posts. The spring loaded plunger is a purchased unit that has an internal spring and a centering point 102A at the lower end thereof that rides in a groove 101C in the pin 101A. This will keep the pin centered and held in the hinge post 100. It can be seen then that if the pin 101B is moved so that the flanges 101 on the cover tend to move upwardly, the pin 101B will have to compress the spring. When the cover is lifted, however, then the spring will be made so that it will urge the pin downwardly toward the lower end of the slot 100B.

When the cover is closed, and the seals on the seal plate engage the respective surfaces, the design is made so that there will be a load on the spring loaded plunger 102 tending to resist movement of the cover away from the base frame 25.

Figure 2:
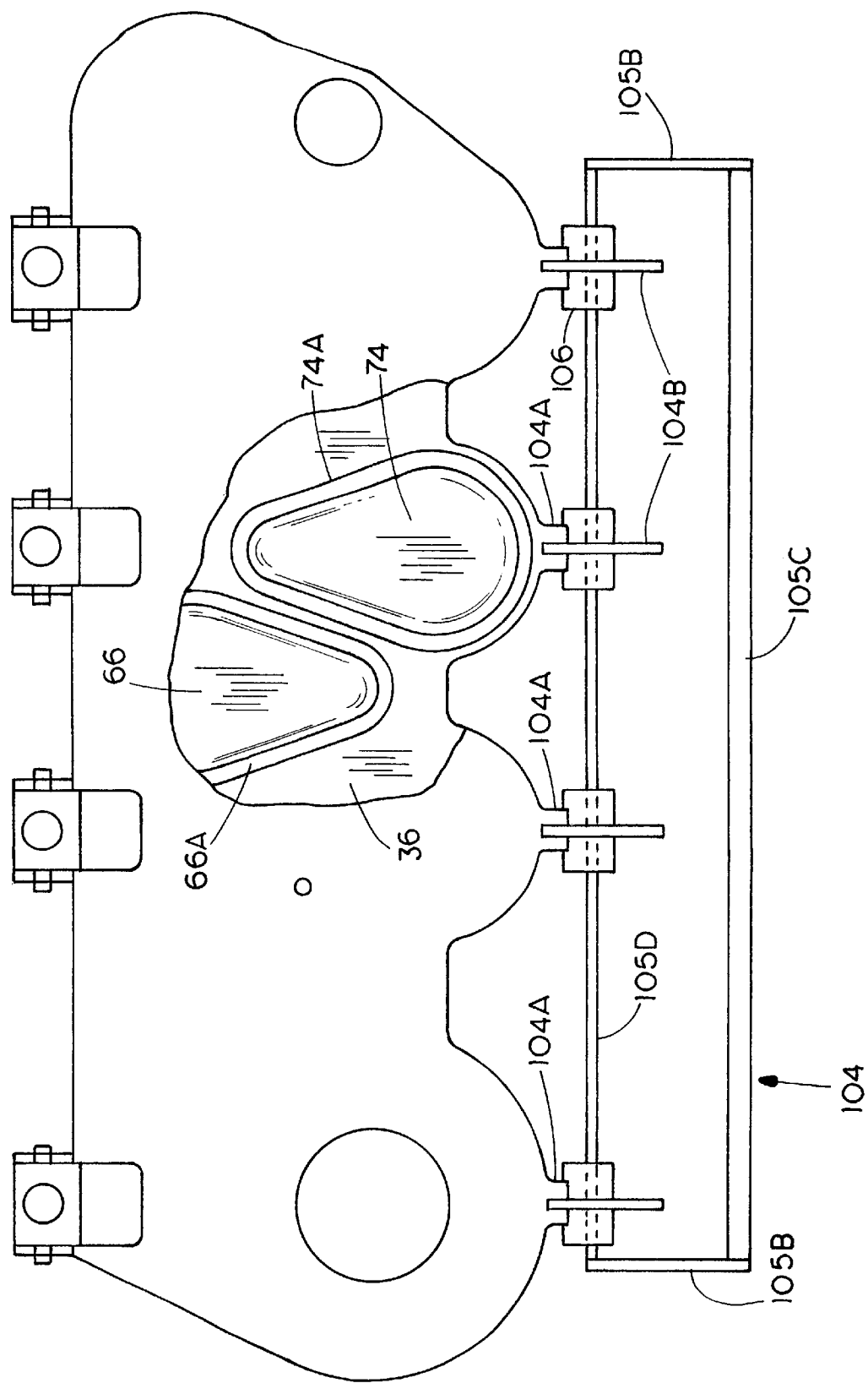
FIG. 2 is a top plan view thereof with parts broken away.

In order to have an adequate compression load on the seals, a cam type latch assembly 104 is utilized, and is shown in FIGS. 2, 4 and 10 primarily. The latch assembly 104 is supported on ears 104A that are on the cover member, through first pivot arms 104B. The hinge members or ears 104A have pins 104C that permit the arms 104B to pivot upwardly and downwardly as shown in dotted lines in FIG. 4, where the solid line position shows the cam latch assembly 104 in locked position, and the dotted line position shows it released.

The arms 104B in turn are pivoted to a latch handle assembly 105, at each of the arms, with a pin 105A positioned so that it will permit pivotal movement of the handle 105. The handle assembly 105 comprises a pair of end arm members 105B, 105B as shown in FIG. 2 that are to the outside of the outer ones of the hinges 104A and first pivot arms 104B. The handle arms 105B are connected with a handle rail 105C that comprises a hand grip, and the handle arms 105B are also joined with a latch bar 105D that is carried so that it will pivot with the arms 105 as they pivot on the pins 105A. There are four of the pins 105A, one at each of the first pivot arms 104B, and the latch bar 105D, extends along the impactor front edge. As shown in FIGS. 4 and 10, the latch bar has a rounded nose portion 105E.

The base flange 25 carries a plurality of latch hooks 106, which as shown in FIGS. 5 and 10 have recesses facing downwardly, and the recesses in the hooks 106 are spaced from a line that passes through the axis of pin 105A and the axis of pin 104C when the latch bar is in its latched position in the hooks 106, as shown in FIG. 4. This forms an over center latch, and it can be seen that the hooks 106 have a surface receive the nose portion 105E and extend parallel to the latch bar 105B.

As shown in FIG. 4, when the latch is in position, the load line of the nose portion 105E is over center so that the unit is held tightly closed, and will not be released accidentally.

The amount of compression of the seals can be regulated by the distance between the pivot of the pins 105A and the center of the nose 105E on the latch bar.

The handle 105C can be moved for release in direction as indicated by the arrow 106D. There is a double pivot about the pins 105A and the pins 104C so that the latch handle can be moved all the way up to a released position as shown in dotted lines in FIG. 4. When the latch is to be closed, it is moved down to a position shown in FIG. 10, where the pivot arms 104B are pivoted downwardly about the pin 104C, but the handle arms 105B are still "cocked" in a ready position so that the latch bar 105D is beneath the hooks 106, but not engaging them. Then, by moving the handle in direction as indicated by the arrow 106E in FIG. 10, it can be seen that the latch bar 105D will tilt upwardly, and come under the hook members 106 into the seat that the nose 105E rests in, and as it does so, it will tend to clamp the cover and the base frame 25 together. It will then go over center as shown in FIG. 4 in order to latch in place.

As can be seen, there are four of the hooks 106 and four of the hinges 104A. The latch provides a positive lock. The cover hinge can be a pin hinge that does not move vertically and comprises hinge pins on the cover and bores for the hinge pins on the base frame. The pins on the cover can be fixed to ears and slip into the bores for pivoting when the cover moves laterally so that upon reverse direction movement the pins can be removed from the base for washing. Also, instead of the latch hooks being on the base frame 25, the hooks can be on the cover, and the pivoting arms and latch bar mounted on the base frame.

As shown in FIG. 1, the base frame 25 has support feet 25F, and at the hinge end, a bracket 108 is provided that can be fixed to the hinge bosses 100, and the bracket 108 has an upright leg 108A that is rigidly attached to the lower portion of the leg, and when the unit is turned up on edge, the bracket 108A will support the impactor assembly 10 with the hinge edge downwardly, and letting it stand in an upright position with the handle extended upwardly.

As can be seen in FIG. 6 and other figures, the bottom surface of the base frame 25 is supported off the supporting surface with the feet legs 25F. The bottoms of the cups clear the supporting surface. This means that when the cover is opened, after the test has been run, tray 36 can be lifted out of the bottom frame, manually or with a fixture. When the tray is lifted all of the cups can be removed as a unit. The cups may be placed either in a separate container and sealed, or moved to another location for direct analysis.

The ability to lift all of the cups at once makes automation easier, because they can be installed in racks and moved as a unit. The cup tray has locating flanges 37 that act as feet when the tray is removed. The locator flanges 37 lap over the edges of the base to keep the tray 36 in place.

The cups also have outwardly tapered side walls so they can be nested and stacked for storage.

The flow paths are shown essentially in FIG. 3, with arrows 99. The flow path is from the inlet to the outlet. The path is divided into segments, forming impaction stages, by the nozzles.

The nozzles and the orifice sizes are selected to provide at least 5 cut points at all desired flow ranges that are between 0.4 $\mu$m and 6.0 $\mu$m. In addition, one stage should provide particles between 5 $\mu$m and 10 $\mu$m. A pressure drop across the impactor of less than 100 inches of water at the maximum flow rate is desired.

The designs for meeting Pharmacopoeial standards of the present invention have fixed nozzles and flow rates between 30 liters per minute and 100 liters per minute. The cut point of particles at the first stage (at the inlet) with a flow rate of 100 liters per minute (a maximum) will provide particles of about 6.0 $\mu$m. The cut point of the last stage at a minimum design flow rate of 30 liters per minute would be 0.50 microns.

The nozzles need to be spaced appropriately, and if they are too close to each other or to the wall of the impactor body, they will tend not to collect particles well. The cluster diameter of the nozzle openings and each of the nozzles is no more than two inches at any stage, which influences the overall design.

The flow range of 30 liters per minute (minimum) to 100 liters per minute is a selected range that is in keeping with hand-held inhalers and other equipment with which this device is to be used.

The impactors of the present invention obtain the desired range of cut points without having interchangeable nozzle plates. While the cut points will shift with flow rates, with 7 stages as shown, followed by a micro orifice filter, the desired range of cut points can be obtained from 5 or more of the nozzle plates.

The micro orifice filter is a nozzle that has a large number of small holes, and takes the place of, a conventional or absolute final filter typically used in impactor designs. The reason for designing the impactor with a micro orifice filter is that it is much easier to recover drug material from a micro orifice filter than from a conventional glass fiber or metallic final filter in manual and automated operations. The micro orifice filter is like an impactor stage with thousands of nozzles, each less than about a hundred microns in diameter.

The micro orifice filter is made to efficiently capture particles of about 0.1 $\mu$m to 0.2 $\mu$m, depending on the flow rate. The smallest particles captured by the micro orifice filter will be approximately ⅓ the size of the smallest particles impacted in the seventh stage of the impactor. Table I that follows shows impactor cut point characteristics obtained with the listed nozzle openings size, for three selected inlet flows in liters per minute. Table I, the "Stage Number" is the orifice plate shown in FIG. 2, for example, at each of the respective numbers.

The micro orifice filter is mounted the same as the nozzles on the seal plate 30 and can be removed for cleaning, as can the nozzles. Any particles in cup 98 will also be used in analysis.

The tables that follow are for illustrative purposes.

TABLE I

Impactor Cut-Point Characteristics

| Inlet Flow (LPM) | Stage Number | Nozzle Diameter (mm) | Number of Nozzles | Cut Point ($\mu$m) |
|---|---|---|---|---|
| 100 | 1-32 | 5.49 | 12 | 6.00 |
| | 2-44 | 3.06 | 24 | 3.49 |
| | 3-56 | 1.96 | 32 | 2.03 |
| | 4-64 | 1.18 | 52 | 1.18 |
| | 5-72 | 0.597 | 152 | 0.689 |
| | 6-80 | 0.317 | 400 | 0.401 |
| | 7-80 | 0.205 | 648 | 0.233 |
| | Micro-Orifice Filter | | 3100 | |
| 60 | 1-32 | 5.49 | 12 | 7.77 |
| | 2-44 | 3.06 | 24 | 4.53 |
| | 3-56 | 1.96 | 32 | 2.65 |

TABLE I-continued

Impactor Cut-Point Characteristics

| Inlet Flow (LPM) | Stage Number | Nozzle Diameter (mm) | Number of Nozzles | Cut Point (μm) |
|---|---|---|---|---|
| | 4-64 | 1.18 | 52 | 1.55 |
| | 5-72 | 0.597 | 152 | 0.916 |
| | 6-80 | 0.317 | 400 | 0.546 |
| | 7-88 | 0.205 | 648 | 0.333 |
| | Micro-Orifice Filter | | 3100 | |
| 30 | 1-32 | 5.49 | 12 | 11.0 |
| | 2-44 | 3.06 | 24 | 6.45 |
| | 3-56 | 1.96 | 32 | 3.78 |
| | 4-64 | 1.18 | 52 | 2.23 |
| | 5-72 | 0.597 | 152 | 1.33 |
| | 6-80 | 0.317 | 400 | 0.808 |
| | 7-88 | 0.205 | 648 | 0.506 |
| | Micro-Orifice Filter | | 3100 | |

Table II shows the Reynolds numbers and cumulative pressure drop for the respective nozzles at different diameters at the different stages shown in Table I.

TABLE II

Impactor Cut-Point Characteristics

| Inlet Flow (LPM) | Stage Number | Nozzle Re | Cumulative Δ (inches of water) |
|---|---|---|---|
| 100 | 1-32 | 2070 | 0.11 |
| | 2-44 | 1860 | 0.41 |
| | 3-56 | 2180 | 1.41 |
| | 4-64 | 2220 | 4.24 |
| | 5-72 | 1510 | 9.43 |
| | 6-80 | 1080 | 18.9 |
| | 7-88 | 1030 | 40.3 |
| | Micro-Orifice Filter | | 88.8 |
| 60 | 1-32 | 1240 | 0.04 |
| | 2-44 | 1120 | 0.15 |
| | 3-56 | 1310 | 0.51 |
| | 4-64 | 1330 | 1.52 |
| | 5-72 | 905 | 3.38 |
| | 6-80 | 647 | 6.75 |
| | 7-88 | 618 | 14.2 |
| | Micro-Orifice Filter | | 30.5 |
| 30 | 1-32 | 622 | 0.01 |
| | 2-44 | 559 | 0.04 |
| | 3-56 | 654 | 0.13 |
| | 4-64 | 666 | 0.38 |
| | 5-72 | 453 | 0.84 |
| | 6-80 | 323 | 1.68 |
| | 7-88 | 309 | 3.52 |
| | Micro-Orifice Filter | | 7.47 |

It can be seen that the particle size cut points for each of the different stages, when having 7 stages, provides 5 stages which are within the range of 0.5 μm to 5.0 μm and one stage between 5.0 μm and 10.0 μm, with some variations in the ranges when single size, nozzles are used across the full range. The nozzles do not have to be changed to obtain the beneficial results.

With the inlet flow of 30 liters per minute, the cut points are essentially within the ranges desired are shown in stages 3–7, that is impactors 56, 64, 72, 80 and 88. When the inlet flow is in the nominal range of 60 liters per minute, where actual flow range may be between 50 liters per minute and 70 liters per minute, where many DPI devices will be tested, there are 5 stage cuts between 0.5 μm and 5.0 μm and one stage between 5.0 μm and 10.0 μm (stages 1–6, namely nozzles 32, 44, 56, 64 and 72). At the high flow of 100 liters per minute, stages 1–6 provide cut points between 0.4 μm and 6.0 μm. While the desired cut point is 0.5 μm, it is important to have one cut below 0.5 μm at the lowest stage, because of the fine particles that some drug companies are developing. 6 microns in stage 1 at 100 liters per minute as shown in Table I is between the 5–10 micron range for one cut point.

Figure 9:
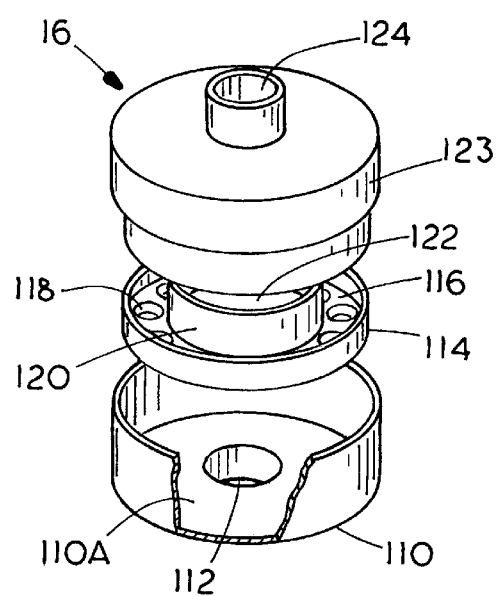
FIG. 9 is an enlarged sectional view of the pre-separator shown in FIG. 8.
Figure 8:
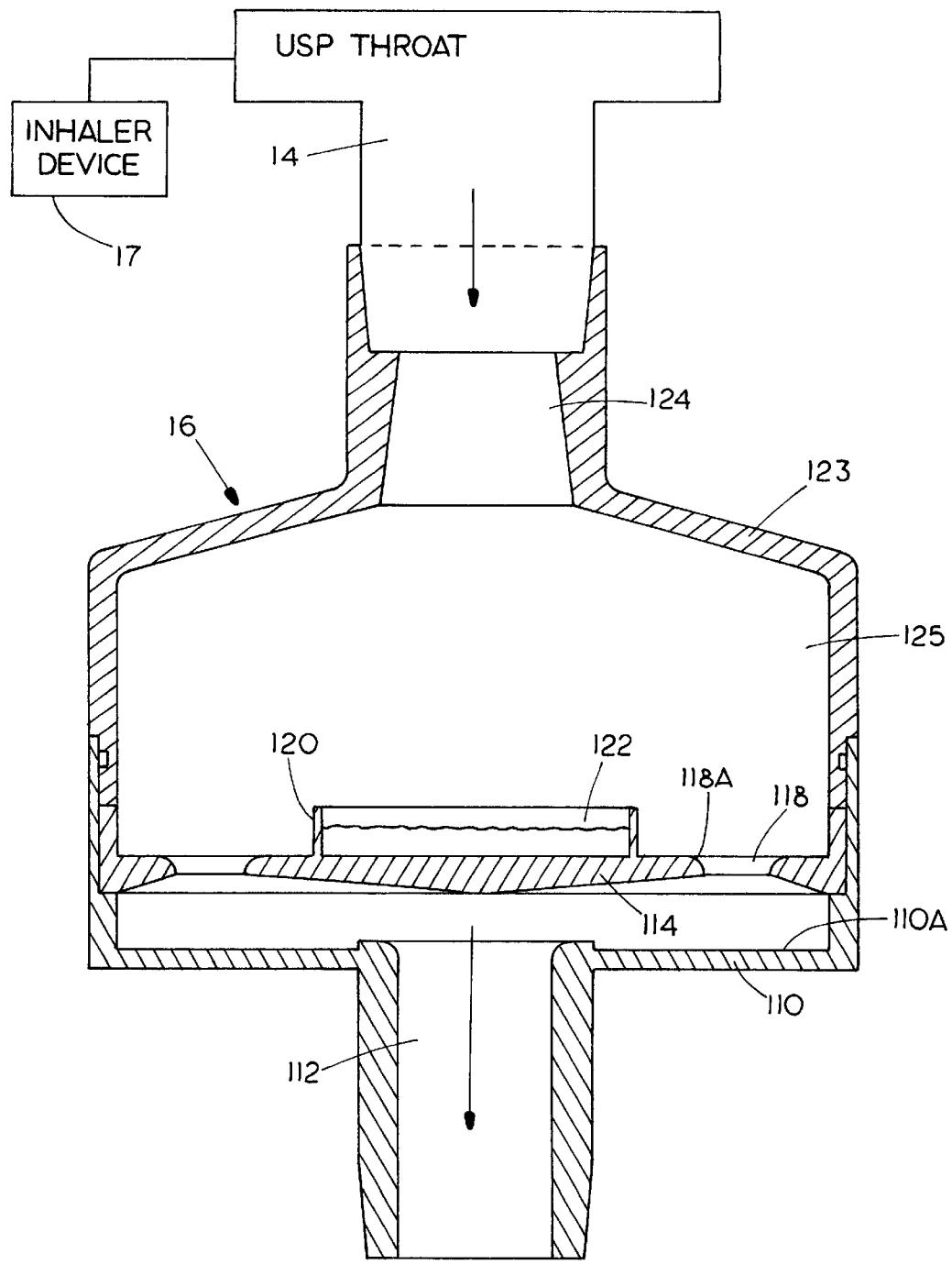
FIG. 8 is an exploded perspective view of a pre-separator that can be used with the present impactor.

The pre-separator 16 is shown in FIG. 8 in exploded view and in FIG. 9 in section. The pre-separator 16 includes a base particle collection plate 110, that has a tube forming an outlet opening 112 leading into the inlet opening 14 of the impactor assembly 10. An impinger plate 114 is mounted above the collection plate 110 in use. The impinger plate includes an annular nozzle 116, with a plurality of openings 118 around the periphery of the impinger plate 114. The openings 118 have tapered inlet ends 118A, and are made so that there are approximately ten openings 118 around the periphery extending through the nozzle 116. The nozzle surrounds a cylindrical wall 120 that forms an impinger chamber 122 within the bounds of the wall 120. The impinger chamber 122 is a small reservoir, and includes a quantity of water that is directly below a tube forming an inlet passage 124 in a cover 123 to which the standard inlet throat is connected. When assembled, the interior chamber 125 around the wall 120 is sealed, and air flowing in through the inlet opening 124 will be directed down onto the surface of the water in the impinger chamber 122, which will cause the heavier particles to separate into the impinger chamber while the flow and smaller particles will pass through the openings 118 of the nozzle 116 toward the surface 110A of the collection plate 110. The cover 123 has an interior surface that tapers toward the inlet passage when inverted, and the under surface of plate 114 also tapers toward opening 118 when the inlet is inverted, so material drains toward the tube forming passage 124.

The impinger chamber 122 is designed so that most particles larger than approximately 20 microns and no smaller than 10 microns will strike the surface of the water when the inlet flow rate is 100 liters per minute. The remaining particles will then pass with the flow through the openings 118. The flow will accelerate in the openings so that all particles larger than 10 microns will collect on the surface 110A below the nozzle. The flow now ideally free of particles larger than 10 microns proceed through the opening 112 into the impactor inlet and to the first stage of the impactor 10.

The pre-separator can be quite small, for example, approximately 4 inches in diameter and 2.6 inches tall excluding the connecting fittings. The openings 118 have a diameter of 0.322 inches.

Approximately 20 ml of water will be in the impinger chamber 122, and the distance from the inlet to the surface of the water will be controlled so that air will flow around the top of the wall 120 and through the openings 118.

Figure 13:
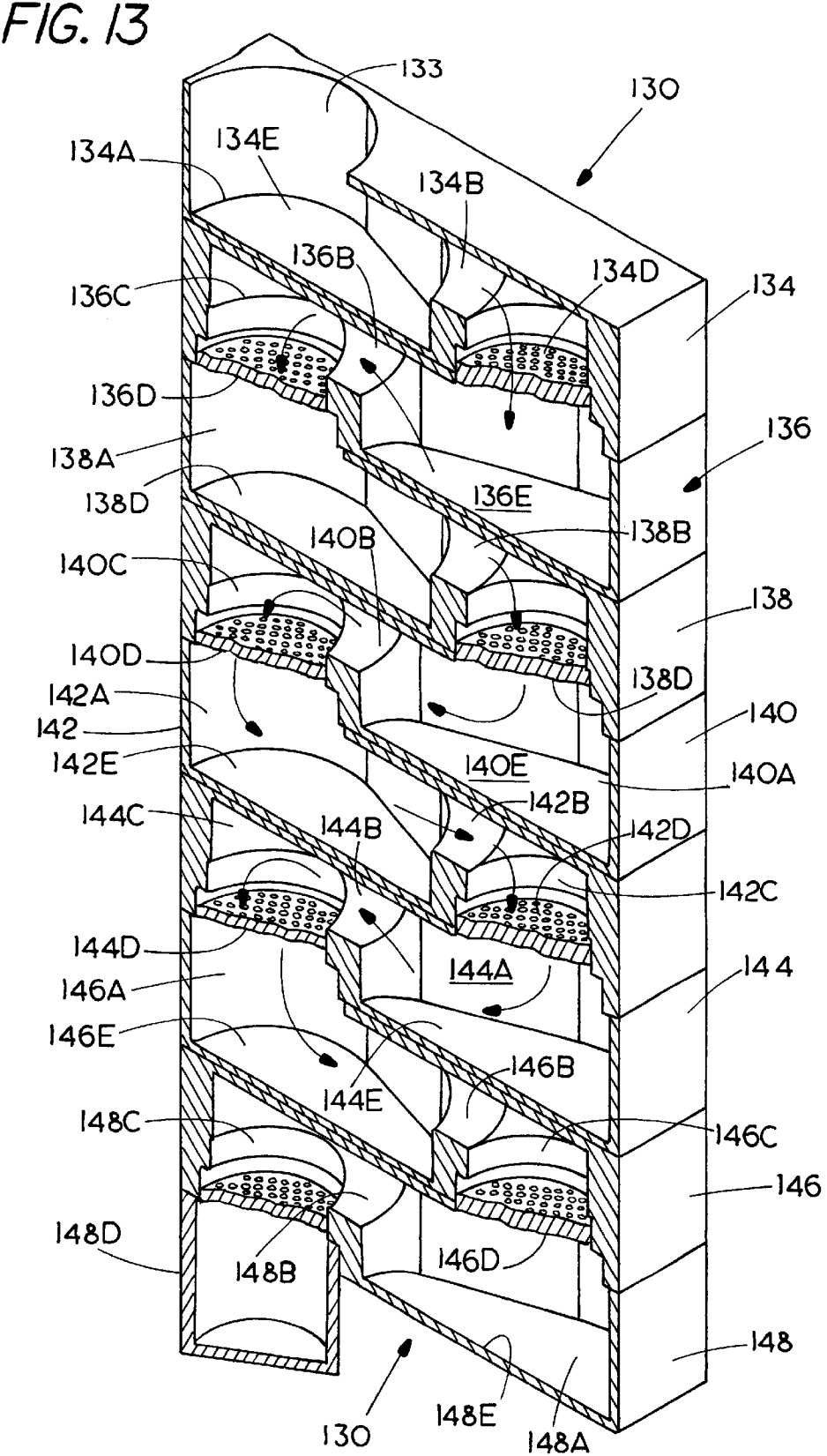
FIG. 13 is a perspective sectional view of a modified form of the invention.
Figure 14:
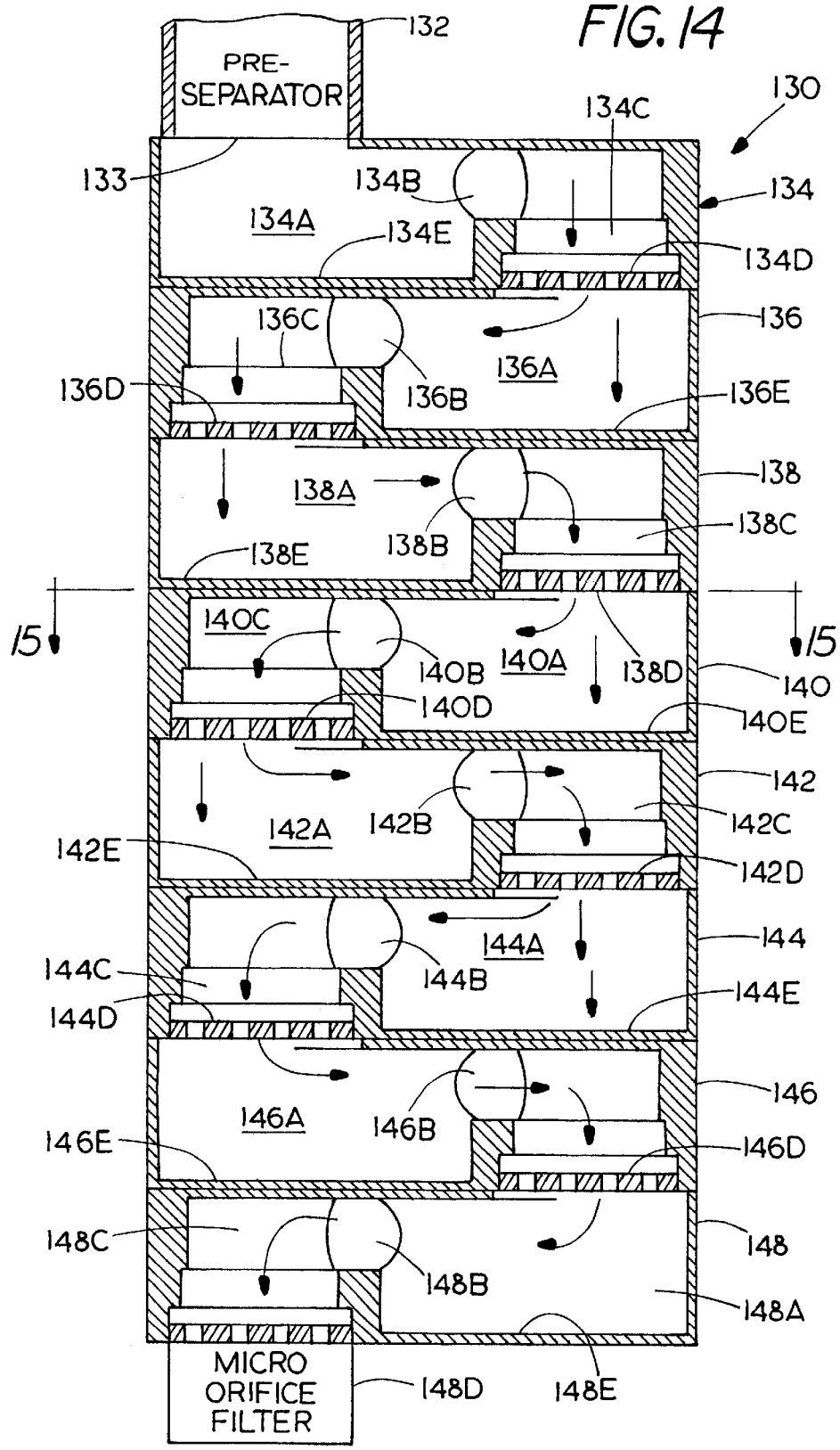
FIG. 14 is a side sectional view of the device of the impactor shown in FIG. 13.
Figure 15:
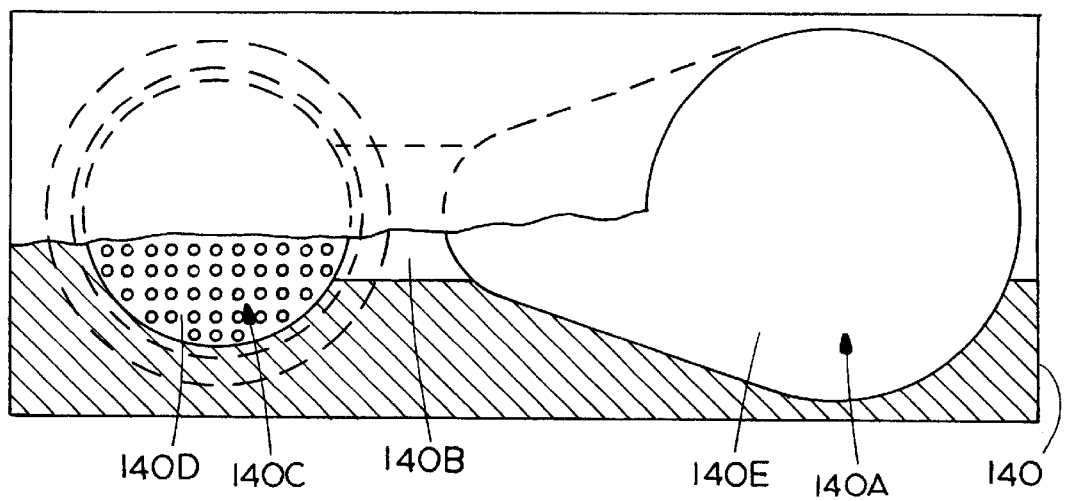
FIG. 15 is a plan view of one section of the impactor in FIG. 14 taken along lines 15—15 in FIG. 14.

In FIGS. 13, 14 and 15, a modified stacked cup design impactor embodying the principles of the present invention is illustrated at 130. The impactor 130 includes several individual stages, one of which is shown in greater detail in FIG. 15. The impactor 130 has an inlet shown schematically at 132 that leads to a first impactor housing 134. The impactor housings are made essentially identical, except that the direction of flow is reversed in the vertically adjacent impactor sections.

The first stage 134 receives the flow from the inlet 132 through a nozzle 133. The first stage housing 134 has a tear drop shaped chamber 134A. The large end comprises an impaction surface 134E, the flow then goes to the narrow end and through a cross or interstage passageway 134B and then through a nozzle passage 134C that has a nozzle plate 134D therein. The nozzle plate 134D is for the second stage impactor and has large openings. The flow will then pass into a second stage impactor housing 136, which forms a chamber 136A that is also tear drop shaped, as can be seen. The chamber 136A receives the flow and has an impactor surface 136E. As indicated by the arrows, the flow goes through a cross or interstage passageway 136B and then into a nozzle passageway 136C and through a third stage nozzle plate 136D that has smaller openings in it, than the second stage nozzle plate 134D as shown in Table I, for example. A different selected size of opening can be selected for different cut points.

The third stage housing 138 includes a third stage chamber 138A through which the flow will pass. The housing 138 has an impaction surface 138E on which particle above the cut point will impinge. The flow enters an interstage passage 138B, and goes into a nozzle passage 138C and through a fourth stage nozzle plate 138D which again has smaller orifices or openings than the third stage nozzle plate 136D.

The flow then passes into a fourth stage housing 140, having a tear drop shaped chamber 140A. It is the fourth stage housing 140 that is shown in FIG. 15. This again is typical of the housings that are shown. The particles above the cut point will impinge on fourth stage impactor surface 140E. The flow passes through an interstage passage 140B, and into a nozzle passageway 140C and through a fifth stage nozzle plate 140D. The opening size in nozzle plate 140D is selected to obtain the desired cut point.

The flow through the nozzle plate 140D enters a fifth stage housing 142, which has a tear drop shaped chamber 142A, and an impactor surface 142E that will serve as a collection plate for particles passing through the nozzle plate 140D that are above the cut off at this stage. The flow goes through an interstage passage 142B and into a nozzle passage 142C. The flow will pass through a further small opening sixth stage nozzle plate 142D. The flow then goes into a sixth stage housing 144, and the sixth stage housing 144 has an impaction surface 144E, in the chamber 144A. The flow then goes through an interstage passage 144B, and through a nozzle passage 144C and then through a seventh stage nozzle 144D into a chamber 146A of a seventh stage housing 146.

The seventh stage has a chamber 146A, with an impactor surface 146E. The flow will pass through an interstage passage 146B, through a nozzle passage 146C and through a micro orifice filter 146D having openings thereon to achieve the desired filtering. The flow will impinge on an impactor plate in housing 148 which has a chamber 148A that receives the flow from the filter 146D. The flow then will pass out through an outlet opening 148C. The micro orifice filter 148D has very fine openings in the nozzle plate as mentioned previously. A microporous filter can have in the range of 3100 openings, as shown in Table I.

The stacked design of FIGS. 13–15 uses the tear shaped chambers, as shown, to insure smooth flow, with little dead volume and thus little chance of having improper cut points.

Figure 16:
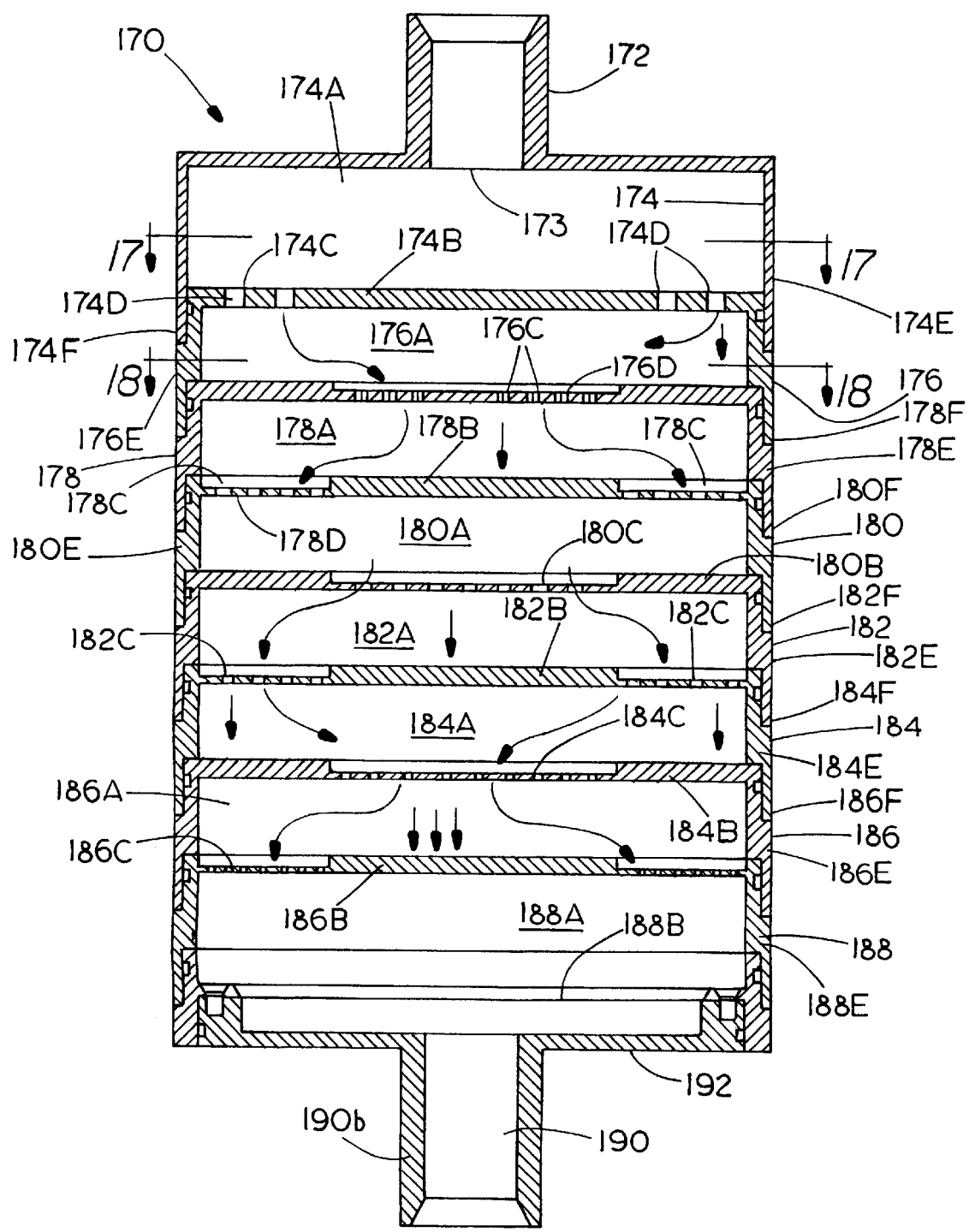
FIG. 16 is a vertical sectional view of a further modified form of the present invention.
Figure 17:
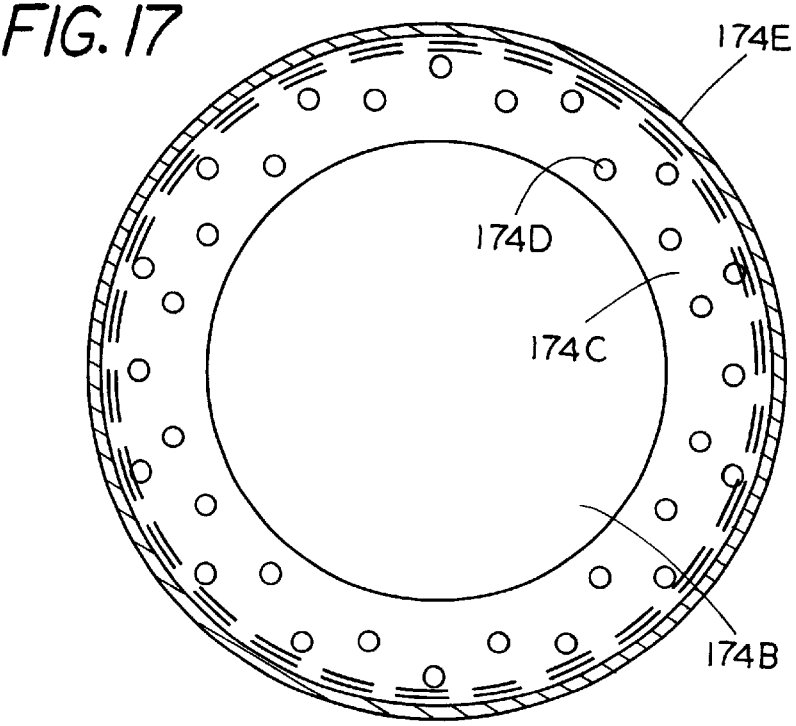
FIG. 17 is a sectional view taken along line 17—17 in FIG. 16.
Figure 18:
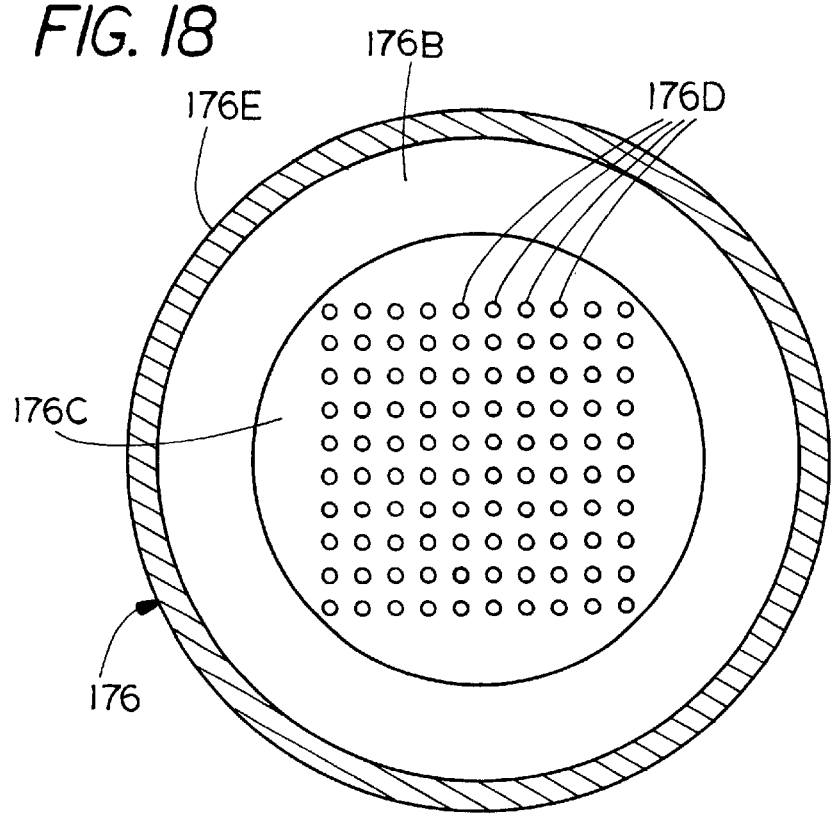
FIG. 18 is a sectional view taken along line 18—18 in FIG. 16.

A further modified form of the invention is shown in FIGS. 16, 17 and 18. An impactor 170 is a cylindrical form and the impactor stages are mounted one above the other, as is common.

The impactor assembly 170 has an inlet tube 172 that connects to a standard inlet as shown, and flow comes through the nozzle 173 into an inlet or first stage housing 174. Housing 174 has an impactor chamber 174A, with a impactor wall or plate portion 174B aligned with the inlet nozzle 173. The flow in this form of the invention is shown in FIG. 16, and large particles will impinge on the surface of impaction plate 174B in the center portions of the wall. The impaction plate 174B is surrounded by an annular nozzle ring 174C that has a plurality of orifices or openings 174D arranged around the periphery adjacent an exterior wall 174E. The flow then will pass through the chamber 174A and through the orifices or openings 174D into a second stage housing 176. The plate 174B and nozzle ring 174C are part of the top wall of the housing 176. The housing 176 is a ring 174E around plate 174B that has a shoulder 174F that receives an end of the housing wall 174E so the two housings nest together.

Housing 176 has a chamber 176A into which the flow through the openings 174D passes. Particles above the cut off size impact on the surface of an annular impaction on wall plate wall 176B. The particles above the cut point will be collected on this annular surface 176B, and the flow in the chamber 176A will then go inwardly toward the center of the chamber 176A and through a center nozzle section 176C in the center portions of the wall, which has a pattern of openings or orifices 176D therein. The orifices 176D are arranged in a square pattern as can be seen in FIG. 17, and the pattern is made of a particular size, generally not more than two inches square, at each of the nozzle plates where the openings are in the center of the impactor plate.

The flow through the nozzle openings 176D will enter into a third impactor stage housing 178, that has a chamber 178A, with an impaction surface on an impaction plate 178B in the center of the chamber, to receive the flow coming through the nozzle openings 176D.

It should be noted that the walls forming the impaction surfaces are supported by the outer wall of the underlying housing, that is wall 174B is supported by 176E, and wall 176B is supported by wall 178E of housing 178. For convenience the impaction surfaces are described as part of the chambers above the walls. Also, the wall 176E has a lower flange 178F that nests on a shoulder 178E of the outer wall 178E of housing 178.

The flow from nozzle 176C then goes outwardly toward the outer periphery of the housing 178, and enters an annular nozzle 178C that has a plurality of openings shown schematically at 178D. The openings in nozzle 178C are smaller than previous nozzles, so that the flow through the openings 178D will pass into a fourth impactor stage housing 180 of the impactor.

The fourth stage 180 has a chamber 180A, and immediately below the annular nozzle 178C, there is an annular impaction surface 180B to receive particles at the cut point for this stage. The flow then goes in toward the center, where there is a center nozzle 180C that has suitable openings, that are of size such that they do not show up in FIG. 16. The flow through the nozzle 180C is through openings such as those shown in FIG. 18. The openings are smaller but still in the square pattern. A shoulder 180F of a peripheral wall 180E supports a lower portion of wall 178E, which nests in place.

The flow through the nozzle 180C then passes into a fifth impactor stage housing 182 that has a chamber 182A, and a wall 182B defining an impaction surface is below nozzle 180C to collect particles at the cut point passing through nozzle 180C. The flow in chamber 182 then moves laterally outwardly to an annular nozzle 182C that again has smaller openings or orifices than the nozzle 180C.

The annular nozzle 182C is arranged as shown in FIG. 17, except that the nozzle openings are smaller. Flow through nozzle 182C enter a sixth housing 184 that has a chamber 184A. The chamber 184A has a lower wall 184B with an annular impaction surface below the annular nozzle 182C. This is an annular wall 184B that forms an impaction surface. The flow then goes toward the center of the wall 184B and through a center nozzle 184C that has small openings that will provide for the desired cut point as the flow enters into a housing 186. The housing 186 has a chamber 186A that receives the flow, and which has a wall 186B having an impaction surface directly below the nozzle 184C, to receive the particles at the cut point for that stage of the impactor. The flow then again goes laterally outwardly into an annular nozzle 186C that has openings leading to a micro filter housing 188 defined by a wall 188E. The flow comes into a chamber 188A, and through a micro filter plate 188B that is filled with small openings as shown in Table I, and then the flow will exit out through an exit passageway 190. The housing walls 182E, 184E, and 186E have shoulders 182F, 184F and 186F to support the housing above it, respectively. The outlet 190b is supported on a cover 192.

The impactor 170 provides the range of cut points as shown in Table I, although the sizes may vary. The annular nozzles and center nozzles alternate between stages.

The impactor 170 can also have the pre-separator assembly on the inlet. The impactor assembly 170 can be disassembled by pulling the telescoping or nesting parts of the housings apart.

Figure 19:
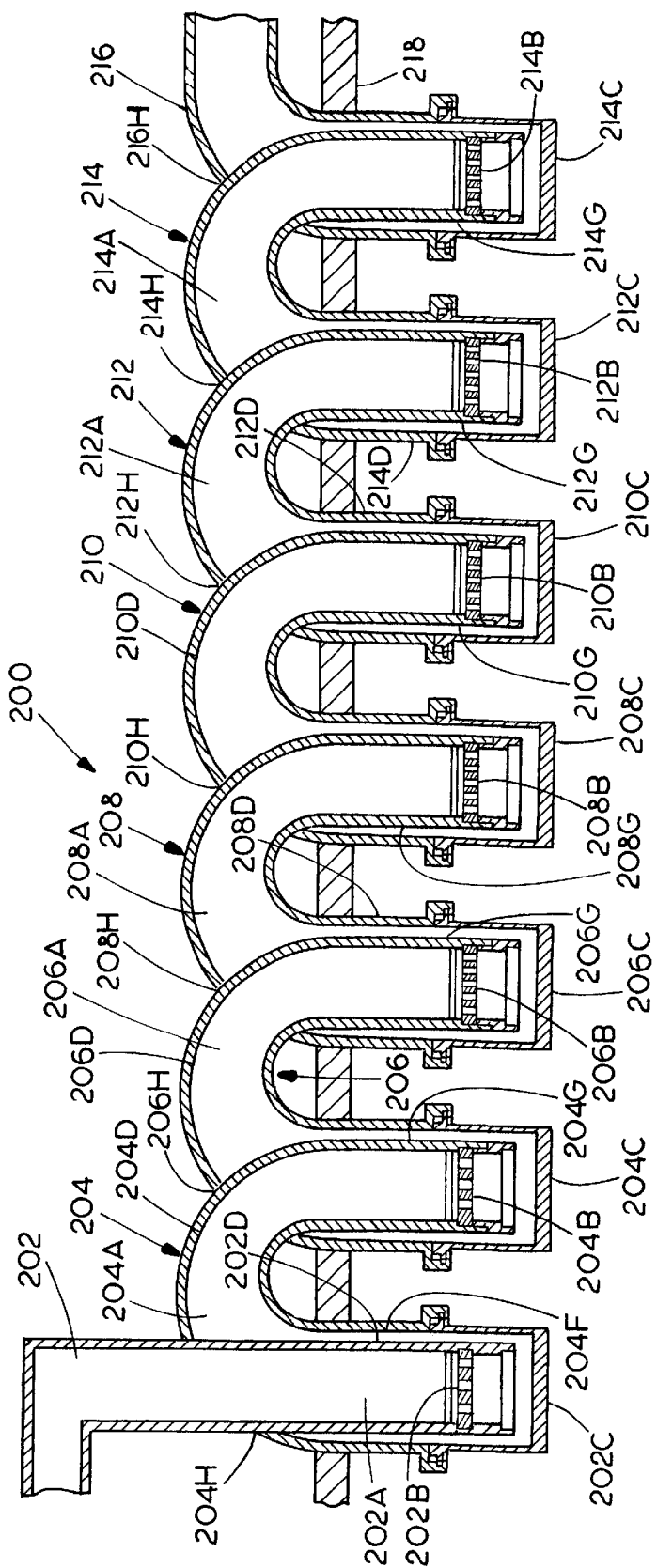
FIG. 19 is a side sectional view of a further modified form of the present invention.

FIG. 19 is a schematic cross sectional view of a modified impactor 200 of the present invention. Impactor 200 is made up of curved cylindrical tubes which places all of the collection cups on a single plane, but yet is compact and space saving. A standard inlet 202 leads through a nozzle passage 202A, and through a first stage nozzle 202B into an impactor chamber comprising a cup 202C that will collect particles above a selected cut size. The cup 202C and the other cups in impactor 200 are removably mounted to permit removal after a test. The cup 202C is larger than and extends annularly around the tube 202D, which forms the passage 202A.

A second impactor stage 204 includes a tube 204D that has a tube section 204F that removably supports the outer edges of the cup 202C, and which surrounds tube section 202D. The cup 202C can be threaded directly to the end of a tube section 204F of tube 204 that forms a passageway to the next impactor stage, or otherwise sealingly, releasably connected in place.

The section 204F forms a passage 204A for carrying flow to a nozzle 204B and into a cup 204C. The tube 204D reduces in diameter in a downstream from the junction region 204H where tube 202 intersects tube 204D. A tube section 204G is of smaller diameter and is directed downwardly. The end of tube section 204G supports nozzle 204B. The cup 204C has an impactor surface that receives and collects the particles from the flow at the selected cut point, and is of large enough in diameter to provide a passage around the reduced size section 204G of tube 204D.

The edge of cup 204C is removably connected to the end of a tube 206D of an impactor stage 206. The tube section 204G intersects tube 206D at a junction 206H and reduces in size downstream from junction 206H at tube section 206G. The tube 206D forms a curved arched passage 206A that directs the flow through tube section 206G and through a nozzle 206B supported in tube section 206G and into a cup 206C. Cup 206C has an impaction surface for receiving particles at that cut point. The cup 206C surrounds and is spaced from tube section 206G and joins larger tube 208D and is supported on an end of a tube 208D is part of a fourth impaction stage tube 208. Tube 208D surrounds the tube section 206G, extends upwardly and curves into a "U" shape and carries the flow around the outer part of the tube 206D through a passageway 208A. A nozzle 208B is in a part of passageway 208A formed by a reduced size tube section 208G and into a cup 208C. The cup 208C forms an impaction surface for receiving the particles of size above the cut point, and is large enough to provide a passage around the tube section 208G and into a surrounding tube 210D of a further impactor stage 210. The cup 208C is removably sealingly mounted on the end of tube section 208D. The tube section passes through tube 210 at a junction 210H.

The tube 210D has an interior passage 210A that directs flow in an arched path. The tube 210 reduces in size in a section 210G that supports a nozzle 210B through which the flow passes into a cup 210C that forms an impaction surface and which is of large enough diameter to join a curved tube 212D of an impaction stage 212. The tube 210D intersects tube 212D at a junction 212H. The tube 212D has an internal passage 212A, that directs flow through a nozzle 212B in reduced diameter tube section 212G, and into a cup 212C, which forms an impaction surface for receiving particles above the cut point. Cup 212C is removably mounted on an end of a tube section 214D and surrounds tube section 212G.

The flow then goes from the cup 212C into a tube 214D of an impaction stage 214. Tube 214D has an internal passage 214A and a reduced size section 214G holding a nozzle 214B leading to a cup 214C. Cup 214C has an impaction surface for collecting particles. The tube 214D is formed as before. The tube section 212G passes into the tube 214D at a junction 214H. The cup 214C is supported on an outlet tube 216 that goes to a microporous filter and vacuum pump. The tube section 214G passes into tube 216 at a junction 214H. These tubes for the impaction stages 202–214, are supported on a support frame 218, of suitable design, and form the necessary impaction surface by having nozzles of the appropriate size for carrying the flows. The tubes 204D–214D all taper smoothly from large diameter sections to the small diameter sections. This causes a variation in flow velocity from each cup to the downstream filter.

All forms of the invention provide for compact arrangements, including the stacked units. The form of the invention shown in FIG. 19 has the common feature of placing the cups all on the single plane so that the cups can easily be put into trays or other supports when they are removed from the respective tubes. The use of the curved, tapered tubes for forming the impaction flow paths permits the cups to not only be in a straight line as shown in FIG. 19, but arranged around a central axis if desired.

All forms of the invention can be used with nozzles having openings as shown in Table I with the approximate pressure drops shown in Table II for the various stages. The accuracy is very high, even with hand-held inhalers where the hand-held generation of the aerosol or active ingredient carrying flow can vary substantially. It should also be noted that predose inhalers can be utilized with the present invention, where a measured amount of a dry powdery agent will be picked up in the flow, such as the breath flow, and this type of material can also be analyzed with the present impactors.

The interstage and other losses of particles are 5% or below with the present invention, which meets established requirements. The impactor provides a sharp cut of particles at each stage of the desired particle classification is thus obtained.

Although the present invention has been described with reference to preferred embodiments, workers skilled in the art will recognize that changes may be made in form and detail without departing from the spirit and scope of the invention.

What is claimed is:

1. An impactor for classifying particles according to size comprising a housing, a flow passageway through said housing, said flow passageway being divided into a plurality of individual passageway sections, a separate nozzle in each passageway section for carrying a flow between individual passageway sections, a particle collection chamber aligned with each nozzle and having an impaction surface to receive flow from the respective nozzle, each particle collection chamber having an output end joining other passageway sections of said flow passageway, said particle collection chamber having a large area portion immediately below its aligned nozzle, and having side walls tapering to a narrow portion at the output end of said collection chamber.

2. The impactor of claim 1, wherein said collection chamber has a wall formed along a radius at the large end and a wall having a substantially smaller radius at the output end, and the side walls being straight wall sections joining the radiused walls at the opposite ends.

3. The impactor of claim 1, wherein each nozzle comprises a nozzle cup having a rim at an open inlet end, a support plate for the nozzle cups, said support plate having an opening for receiving a rim of the respective nozzle cup, and a support rim formed in the opening for engaging the rim on the respective nozzle cup to support it in a known position.

4. The impactor of claim 3, wherein said opening has a surface that provides a seal around a periphery of the respective nozzle cup.

5. The impactor of claim 3, wherein each nozzle cup overlies a collection chamber and has a nozzle wall positioned at a selected distance from the impaction surface of the collection chamber.

6. The impactor of claim 1, wherein said collection chamber comprises a removable cup, said removable cup having a peripheral flange, and a cup tray for supporting said removable cup, said cup tray being removably mounted in said impactor.

7. The impactor of claim 1, wherein there are a plurality of collection chambers, each of said collection chambers having a wide end for receiving flow from a nozzle, and a narrow end joining other portions of the flow passageway which form flow path sections, said collection chambers being supported substantially on a plane, the narrow ends of the chambers overlapping, with the narrow end of each chamber being adjacent the wide end of an adjacent chamber so that the collection chambers nest together.

8. The impactor of claim 7, wherein said collection chambers are supported in a base portion of the housing, a cover portion of the housing hingedly connected to the base portion along one edge thereof, a portion of each flow path section between individual collection chambers being defined in said cover portion.

9. The impactor of claim 8, wherein the portions of the flow path section defined in the cover extend in a transverse direction to a line extending from the wide ends to the narrow ends of the collection chambers.

10. The impactor of claim 9, and a seal plate between the base portion and the cover portion, said seal plate having sealing members surrounding the collection chambers on one side of the seal plate, and second sealing members surrounding the portions of the flow path sections defined in the cover portion on the other side of the seal plate.

11. The impactor of claim 10 and a latch for securing the base portion and the cover portion together, with the seal plate positioned between the base portion and cover portion, said seals on seal plate compressing as the latch is secured.

12. The impactor of claim 11, wherein the hinge connection between the base portion and the cover portion includes a slot on the base portion, the hinge comprising a hinge pin on the cover portion, a spring loading the hinge pin on the cover portion in a first direction in the slot, and the hinge pin moving in a second direction against the force of said spring when the latch is secured and the seal members are compressed.

13. An impactor comprising a housing, said housing having an inlet and an outlet, and a flow path through the housing, said flow path being divided into at least two flow segments, a nozzle between the flow segments, a collection chamber for receiving flow from the nozzle and collecting particles that are carried in the flow, the improvement comprising a pre-separator at the inlet of the housing, said pre-separator including a chamber having an inlet tube and an outlet tube, and having tapered internal surfaces that taper toward one of the tubes for permitting draining of material on the interior of the pre-separator.

14. The impactor of claim 13, wherein said pre-separator includes a collection tank aligned with the inlet opening such that flow impinges on liquid in said collection tank, and before passing to the outlet.

15. The pre-separator of claim 14 and an annular nozzle plate positioned to receive flow from the tank, said flow passing through said nozzle plate to the outlet.

16. The impactor of claim 13, wherein said pre-separator has an inlet adapted to receive aerosols generated by a hand-held inhaler.

17. An impactor for classifying particles according to size, comprising a support, a flow passage defined relative to said support, said flow passage being divided into a plurality of individual passageway sections, a separate nozzle in each passageway section for carrying the flow between the passageway sections, a particle collection chamber aligned with each nozzle and having an impaction surface to receive flow from the respective nozzle, each chamber having an output portion joining other parts of a downstream flow passage, the particle collection chambers having support walls lying substantially on a common plane, wherein the passageway sections comprise tubes that taper in size between each impaction chamber and a next subsequent impaction chamber in the flow path.

18. The impactor of claim 17, wherein said tubes are formed in a generally U-shaped, and the taper of the tubes extends to a smaller diameter section that carries a nozzle for the next subsequent section, the nozzles facing in a downward direction.

19. An impactor for classifying particles according to size comprising a housing, a flow passageway through said housing, said flow passageway being divided into a plurality of individual passageway sections, a separate nozzle in each passageway section for carrying a flow between individual passageway sections, a particle collection chamber aligned with each nozzle and having an impaction surface to receive flow from the respective nozzle at an inlet end formed with an upright wall portion having a large radius to form the inlet end and carrying flow to a wall portion formed in a smaller radius at an output end, the collection chambers being positioned side-by-side and so the large radius inlet end of one collection chamber overlaps and is adjacent to a small radius outlet end of a next adjacent collection chamber.

20. A cup for use in a particle classification impactor having flow carrying nozzles, the cup having a bottom wall forming an impaction surface, and having a peripheral wall forming an open top chamber, the cups have a wide end for receiving flow from a flow nozzle, and a narrow end and forming a flow path through the cup from the wide end to the narrow end, said cups thereby having generally a tear drop shaped open top.

21. The cup of claim 20, wherein the cup has a generally planar peripheral flange extending outwardly from the peripheral wall.

22. An impactor for classifying particles according to size comprising a housing, a flow passageway through said housing, the flow passageway being divided into a plurality of individual passageways sections, a plurality of particle collection cups, one aligned with each nozzle, the cups forming portions of the flow passageway sections, and each of the cups having a peripheral support flange around the periphery thereof, said housing including a base portion and an openable cover, and a tray positioned between the base portion and the cover, said tray having openings corresponding to the shape of the cups, and the peripheral flange being supported on the tray such that a plurality of the cups can be moved by lifting the tray when the cover is opened.

23. The impactor of claim 22, wherein said cover is hingedly mounted to said base portion, the cups having cup portions extending through the tray, and said base portion having openings for receiving the cup portions extending through the tray, said cover being closeable over the cups and tray for forming the flow passageways.

24. The impactor of claim 23, wherein said cover has recesses extending between cups for forming cover portions of the flow passageway sections, and seal members surrounding the cups for sealing the flow passageway sections.

25. The impactor of claim 23, wherein said cups have peripheral flanges that are supported on said tray around surfaces of the tray forming openings for the cup.

* * * * *